United States Patent
Misske et al.

(10) Patent No.: US 9,562,054 B2
(45) Date of Patent: Feb. 7, 2017

(54) PROCESS FOR PREPARING ISOSORBIDE ETHOXYLATE DI(METH)ACRYLATE

(71) Applicant: BASF SE, Ludwigshafen am Rhein (DE)

(72) Inventors: Andrea Misske, Speyer (DE); Friederike Fleischhaker, Ludwigshafen (DE); Christoph Fleckenstein, Freigericht-Somborn (DE); Martin Kaller, Mannheim (DE); Ulrik Stengel, Birkenau (DE); Mathieu Blanchot, Lambsheim (DE); Claudia Stoer, Duesseldorf (DE); Ritesh Nair, Heidelberg (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/051,974

(22) Filed: Feb. 24, 2016

(65) Prior Publication Data

US 2016/0251370 A1 Sep. 1, 2016

Related U.S. Application Data

(60) Provisional application No. 62/120,917, filed on Feb. 26, 2015.

(51) Int. Cl.
| | |
|---|---|
| *C07D 493/04* | (2006.01) |
| *C08F 24/00* | (2006.01) |
| *C09J 4/06* | (2006.01) |
| *C08F 222/10* | (2006.01) |
| *C09J 4/00* | (2006.01) |

(52) U.S. Cl.
CPC ....... *C07D 493/04* (2013.01); *C08F 222/1006* (2013.01); *C09J 4/00* (2013.01); *C09J 4/06* (2013.01)

(58) Field of Classification Search
CPC .............................. C07D 493/04; C08F 24/00
USPC ................... 526/75, 268; 549/464; 560/204
See application file for complete search history.

(56) References Cited

U.S. PATENT DOCUMENTS

| | | | |
|---|---|---|---|
| 5,288,767 A | 2/1994 | Cramer et al. | |
| 2013/0178592 A1* | 7/2013 | Bette | C08F 20/06 526/233 |

FOREIGN PATENT DOCUMENTS

| | | |
|---|---|---|
| DE | 2 317 226 A1 | 10/1974 |
| DE | 41 31 458 A1 | 3/1993 |
| EP | 2 174 941 A1 | 4/2016 |
| JP | 2011-84535 A * | 4/2011 ........... C07D 493/04 |
| WO | WO 2009/080380 A2 | 7/2009 |

OTHER PUBLICATIONS

Machine translation of JP 2011-84535A, published Apr. 2011.*
Lukaszczyk et al., "Synthesis and Characterization of Low Viscosity Dimethacrylate Resin Based on Isosorbide," Journal of Applied Polymer Science, 2013, 2514-2522.*
International Search Report issued May 4, 2016 in PCT/EP2016/053857 (with English translation of categories).
Zhila Vazifehasl, et al., "New Series of Dimethacrylate-Based Monomers on Isosorbide as a Dental Material: Synthesis and Characterization" International Journal of Composite Materials, vol. 3, No. 4, XP55268012, Jan. 1, 2013, pp. 100-107.

* cited by examiner

*Primary Examiner* — Fred M Teskin
(74) *Attorney, Agent, or Firm* — Oblon, McClelland, Maier & Neustadt, L.L.P.

(57) ABSTRACT

A process for preparing isosorbide ethoxylate di(meth)acrylate by transesterifying alkyl (meth)acrylate with isosorbide ethoxylate, comprising the steps of:
(i) ethoxylating isosorbide to give isosorbide ethoxylate,
(ii) reacting alkyl (meth)acrylate with isosorbide ethoxylate in the presence of potassium phosphate as catalyst and a stabilizer and in the presence of an azeotroping agent which forms an azeotrope with the alcohol bound in the alkyl (meth)acrylate,
(iii) continuously distilling off the azeotrope of azeotroping agent and alcohol, wherein steps (ii) and (iii) are conducted simultaneously until the isosorbide ethoxylate has been essentially fully converted,
(iv) removing the catalyst from the product mixture comprising isosorbide ethoxylate di(meth)acrylate,
(v) distilling unconverted alkyl (meth)acrylate and azeotroping agent out of the product mixture.

9 Claims, No Drawings

PROCESS FOR PREPARING ISOSORBIDE ETHOXYLATE DI(METH)ACRYLATE

FIELD OF INVENTION

The invention relates to a process for preparing isosorbide ethoxylate di(meth)acrylate by transesterifying alkyl (meth) acrylate with isosorbide ethoxylate, to the isosorbide ethoxylate di(meth)acrylate itself and to the use thereof.

DISCUSSION OF THE BACKGROUND

E2BADMA (dimethacrylate of bisphenol A alkoxylated with 2 ethylene oxide units in each case) and E3BADMA (dimethacrylate of bisphenol A alkoxylated with 3 ethylene oxide units in each case) are bisphenol A-based dimethacrylates which are used as crosslinkers, for example in coatings and mixtures for drillholes. They are notable for a rapid reaction time which leads to partial load-bearing capacity of 2-pack mixtures even after a short time and attainment of the final tensile strength after a few hours. In addition, they have a high polymer density with a very good cohesion/adhesion ratio, good crystallization resistance with simultaneously low shrinkage and a low tendency to embrittlement, and high wetting power in order to assure good creeping capacity in capillary cracks.

DE 41 31 458 A1 discloses two-pack adhesive compositions for chemical securing technology, comprising a synthetic resin comprising the di(meth)acrylate of an alkoxylated bisphenol and a hardener for the synthetic resin.

For particular applications, bisphenol A-free crosslinkers having a similar profile of properties are being sought.

Isosorbide is a diol based on renewable raw materials and, in structural terms, is an alternative to bisphenol A, since it has a similarly rigid base structure.

One means of preparing di(meth)acrylates from isosorbide is the esterification of isosorbide with (meth)acrylic acid or the transesterification of methyl acrylate, ethyl acrylate or methyl methacrylate with isosorbide in the presence of suitable catalysts. Both OH groups of isosorbide are secondary OH groups having comparatively low reactivity, and the relative reactivities of the two OH groups are additionally very different. Thus, incomplete conversion is to be expected.

DE 2 317 226 A1 discloses a method of preparing (meth)acrylic esters from a mixture of $C_{10}$-$C_{18}$ alkanols by transesterification of methyl (meth)acrylate in the presence of titanium alkoxide as catalyst and 2,6-di-tert-butylparacresol (TBC) as stabilizer. This method is carried out in the presence of activated carbon. Once the reaction has ended, water is added to hydrolyze the titanium alkoxide to titanium hydroxide/oxide which adsorbs onto the activated carbon. The solid is filtered off and the reaction product is subjected to a steam distillation.

WO 2009/080380 discloses a process for preparing methacrylates of $C_6$-$C_{22}$ alcohols by transesterifying methyl (meth)acrylate with the appropriate alcohols in the presence of titanium alkoxide as catalyst. In example 1, methyl methacrylate is reacted with 2-ethylhexanol in the presence of hydroquinone monomethyl ether (MEHQ) as stabilizer and tetraisopropyl titanate as catalyst. An azeotropic mixture of methanol/methyl methacrylate is distilled off. After distilling off unconverted methyl methacrylate, the catalyst-comprising 2-ethylhexyl methacrylate is subjected to a purifying distillation under reduced pressure (about 30 mbar). This affords 2-ethylhexyl methacrylate in 99.4% purity.

DETAILED DESCRIPTION OF THE INVENTION

It is an object of the invention to provide a process for preparing (meth)acrylates of isosorbide in which by-products are formed only to a minor degree.

The object is achieved by a process for preparing isosorbide ethoxylate di(meth)acrylate by transesterifying alkyl (meth)acrylate with isosorbide ethoxylate, comprising the steps of:
(i) ethoxylating isosorbide to give isosorbide ethoxylate,
(ii) reacting alkyl (meth)acrylate with isosorbide ethoxylate in the presence of potassium phosphate as catalyst and a stabilizer in the presence of an azeotroping agent which forms an azeotrope with the alcohol bound in the alkyl (meth)acrylate,
(iii) continuously distilling off the azeotrope of azeotroping agent and alcohol, wherein steps (ii) and (iii) are conducted simultaneously until the isosorbide ethoxylate has been essentially fully converted,
(iv) removing the catalyst from the product mixture comprising isosorbide ethoxylate di(meth)acrylate,
(v) distilling unconverted alkyl (meth)acrylate and azeotroping agent out of the product mixture.

It has been found that, surprisingly, transesterification of alkyl (meth)acrylate with isosorbide ethoxylate in the presence of potassium phosphate as catalyst forms isosorbide ethoxylate di(meth)acrylate in high yields.

Ethoxylation of isosorbide to give isosorbide ethoxylate partly converts the comparatively unreactive secondary OH groups of different reactivity in isosorbide to reactive primary OH groups of essentially the same reactivity. These have very good reactivity with alkyl (meth)acrylate in the presence of potassium phosphate as catalyst to give isosorbide ethoxylate di(meth)acrylate.

Alkoxylation with only a few equivalents of EO (e.g. 3 equivalent of EO) affords an alcohol mixture which still has a proportion of secondary OH groups. If EO is used in a greater molar ratio, the proportion of primary alcohol rises, but longer polyalkylene oxide chains also form. This affects the properties of the crosslinker, which then has a more flexible structure.

The degree of conversion of the alcohol mixture formed by the alkoxylation can be analyzed most simply via the determination of the OH number. This indicates the content of OH groups as a cumulative parameter in the unit mg KOH/g of substance and can be converted to percent by weight assuming a particular molar mass of the alcohol.

The content of alcohols, determined via the OH number and calculated, for example, as isosorbide*3EO, in the product obtained after step (v) is preferably <2% by weight, more preferably <1% by weight.

In addition, the product obtained after step (v) may still comprise traces of azeotroping agent and alkyl (meth) acrylate. These may be present in the product obtained after step (v) in total amounts of up to 2% by weight, preferably up to 1% by weight.

The amount of all the secondary components (isosorbide ethoxylate, monoesters of isosorbide ethoxylate, azeotroping agent and alkyl (meth)acrylate, with determination of isosorbide ethoxylate and monoesters of isosorbide ethoxylate via the OH number and calculation as isosorbide*3E0) in the product obtained after step (v) is generally up to 4% by weight, preferably up to 2% by weight.

In a first step (i), isosorbide is ethoxylated with ethylene oxide to give isosorbide ethoxylate. In general, 2 to 4 mol of ethylene oxide, preferably 2 to 3.5 mol of ethylene oxide, are converted per mole of isosorbide ethoxylate.

The ethoxylation can be conducted with gaseous ethylene oxide in the presence of basic or acidic catalysts at a pressure of 100 to 500 kPa and preferably at temperatures of 120 to 220° C., as described, for example, in EP 2 174 941. Suitable basic catalysts are, for example, NaOH or KOH or sodium methoxide or potassium methoxide.

In step (ii), alkyl (meth)acrylate is reacted with isosorbide ethoxylate in the presence of potassium phosphate as catalyst and a stabilizer in the presence of an azeotroping agent which forms an azeotrope with the alcohol bound in the alkyl (meth)acrylate, with simultaneous distillative removal of the azeotrope of azeotroping agent and alcohol in step (iii) until isosorbide ethoxylate has been essentially fully converted. The transesterification thus consists of steps (ii) and (iii).

Suitable alkyl (meth)acrylates are the $C_1$-$C_4$-alkyl (meth)acrylates. In general, methyl (meth)acrylate or ethyl (meth)acrylate is used, with release of methanol or ethanol as alcohols in the transesterification reaction.

The reaction of alkyl (meth)acrylate with isosorbide ethoxylate is effected in the presence of solid suspended potassium phosphate as catalyst.

The reaction of alkyl (meth)acrylate with isosorbide ethoxylate is additionally effected in the presence of one or more stabilizers (polymerization inhibitors). Examples of suitable stabilizers are N-oxides (nitroxyl or N-oxyl radicals, i.e., compounds bearing at least one N—O group), for example 4-hydroxy-2,2,6,6-tetramethylpiperidine N-oxyl, 4-oxo-2,2,6,6-tetramethylpiperidine N-oxyl, 4-acetoxy-2,2,6,6-tetramethylpiperidine N-oxyl, 2,2,6,6-tetramethylpiperidine N-oxyl, bis(1-oxyl-2,2,6,6-tetramethylpiperidin-4-yl) sebacate, 4,4',4"-tris(2,2,6,6-tetramethylpiperidine N-oxyl) phosphite or 3-oxo-2,2,5,5-tetramethylpyrrolidine N-oxyl; mono- or polyhydric phenols which may bear one or more alkyl groups, for example alkylphenols, for example o-, m- or p-cresol (methylphenol), 2-tert-butylphenol, 4-tert-butylphenol, 2,4-di-tert-butylphenol, 2-methyl-4-tert-butylphenol, 2-tert-butyl-4-methylphenol, 2,6-tert-butyl-4-methylphenol, 4-tert-butyl-2,6-dimethylphenol or 6-tert-butyl-2,4-dimethylphenol; quinones, for example hydroquinone, hydroquinone monomethyl ether, 2-methylhydroquinone or 2,5-di-tert-butylhydroquinone; hydroxyphenols, for example catechol (1,2-dihydroxybenzene) or benzoquinone; aminophenols, for example p-aminophenol; nitrosophenols, for example p-nitrosophenol; alkoxyphenols, for example 2-methoxyphenol (guaiacol, catechol monomethyl ether), 2-ethoxyphenol, 2-isopropoxyphenol, 4-methoxyphenol (hydroquinone monomethyl ether), mono- or di-tert-butyl-4-methoxyphenol; tocopherols, for example a-tocopherol and 2,3-dihydro-2,2-dimethyl-7-hydroxybenzofuran (2,2-dimethyl-7-hydroxycoumaran), aromatic amines, for example N,N-diphenylamine or N-nitrosodiphenylamine; phenylenediamines, for example N,N'-dialkyl-p-phenylenediamine where the alkyl radicals may be the same or different and each independently consist of 1 to 4 carbon atoms and may be straight-chain or branched, for example N,N'-dimethyl-p-phenylenediamine or N,N'-diethyl-p-phenylenediamine, hydroxylamines, for example N,N-diethylhydroxylamine, imines, for example methyl ethyl imine or methylene violet, sulfonamides, for example N-methyl-4-toluenesulfonamide or N-tert-butyl-4-toluenesulfonamide, oximes such as aldoximes, ketoximes or amide oximes, for example diethyl ketoxime, methyl ethyl ketoxime or salicylaldoxime, phosphorus compounds, for example triphenylphosphine, triphenyl phosphite, triethyl phosphite, hypophosphorous acid or alkyl esters of the phosphorous acids; sulfur compounds, for example diphenyl sulfide or phenothiazine, or mixtures thereof.

Preference is given to hydroquinone, hydroquinone monomethyl ether, phenothiazine, 4-hydroxy-2,2,6,6-tetramethylpiperidine N-oxyl, 4-oxo-2,2,6,6-tetramethylpiperidine N-oxyl, 2-tert-butylphenol, 4-tert-butylphenol, 2,4-di-tert-butylphenol, 2-tert-butyl-4-methylphenol, 6-tert-butyl-2,4-dimethylphenol, 2,6-di-tert-butyl-4-methylphenol and 2-methyl-4-tert-butylphenol.

Particular preference is given to hydroquinone monomethyl ether (MeHQ).

Advantageously, oxygen may additionally be used as a polymerization inhibitor.

For further stabilization, an oxygenous gas, preferably air or a mixture of air and nitrogen (lean air), may be present.

The transesterification reaction (steps (ii) and (iii)) is generally conducted at a temperature of 60° C. to 140° C., preferably 70° C. to 110° C. In the course of this, an azeotrope of azeotroping agent and alcohol is distilled off continuously.

Suitable azeotroping agents which form an azeotropically boiling mixture with methanol or ethanol are, first of all, methyl acrylate and methyl methacrylate and also ethyl acrylate and ethyl methacrylate themselves. Suitable separate azeotroping agents include cyclohexane, methylcyclohexane, benzene, toluene, hexanes and heptanes, and mixtures thereof. Preference is given to methyl acrylate, methyl methacrylate, ethyl acrylate and ethyl methacrylate, and to mixtures of these with n-heptane and cyclohexane. The term azeotroping agent in this context encompasses the reactant itself and any separate solvent additionally used.

In a preferred embodiment, no separate solvent is used as azeotroping agent. In this case, the alkyl (meth)acrylate reactant itself serves as azeotroping agent.

The azeotroping agent may subsequently be replenished in the reactor. For this purpose, the azeotropic mixture of alchohol and azeotroping agent, in a preferred embodiment, is distilled off by means of a suitable column, stirred with water in a mixing vessel and then transferred into a phase separator, wherein the alcohol, generally methanol or ethanol, dissolves in water and the organic phase separates out as the upper layer. The organic phase is preferably returned to the reaction mixture via the top of the column and hence recirculated save for small losses. It is alternatively also possible to add fresh azeotroping agent and work up the azeotroping agent/alcohol mixture in a separate step or to wholly or partly dispense with replenishment of the azeotroping agent.

In general, alkyl (meth)acrylate is used in a stoichiometric excess. Preferably, the excess of methyl (meth)acrylate per hydroxyl group to be esterified is 5 to 1000 mol %, more preferably 50 to 500 mol % and especially 100 to 400 mol %.

The catalyst is used in a concentration of 0.1-10 mol % based on the amount of the isosorbide ethoxylate used, preferably in a concentration of 0.1 to 5 mol %.

The transesterification may be conducted at atmospheric pressure, but also under elevated pressure or reduced pressure. It is generally conducted at 300 to 1000 mbar, preferably at 300 to 700 mbar (atmospheric pressure=1000 mbar). The reaction time is generally 1 to 24 hours, preferably 3 to 18 hours and more preferably 3 to 10 hours. The transesterification (steps (ii) and (iii)) can be effected continuously, for example in a stirred tank cascade, or batchwise.

The reaction may be conducted in all reactors suitable for a reaction of this type. Such reactors are known to those skilled in the art. The reaction is preferably effected in a stirred tank reactor.

The batch can be mixed using any desired apparatuses, for example stirring apparatuses. The mixing can also be effected by feeding in a gas, preferably an oxygen-containing gas.

The alcohol formed, generally methanol or ethanol, is removed continuously or stepwise in a manner known per se by azeotropic distillation in the presence of an azeotroping agent. In addition, methanol may also be removed by stripping with a gas.

In a preferred embodiment, alcohol is removed from the azeotrope of azeotroping agent and alcohol distilled off in step (iii) by washing with water and the azeotroping agent is recycled into the reaction vessel.

Steps (ii) and (iii) are conducted until the isosorbide ethoxylate used has been essentially fully converted. This is the case when isosorbide ethoxylate has been converted to the diester to an extent of 95%, preferably to an extent of 97% and more preferably to an extent of 98%. The degree of conversion can be analyzed most simply via the determination of the OH number. This indicates the content of OH groups as a cumulative parameter in the unit mg KOH/g of substance and can be converted to percent by weight assuming a particular molar mass of the alcohol.

In step (iv), the solid catalyst is separated from the product mixture comprising isosorbide ethoxylate di(meth)acrylate, for example by filtration or centrifugation.

The filtration can be conducted, for example, with a pressure suction filter. In process engineering terms, for a filtration in the process of the invention, it is possible to use any filtration methods and apparatuses known per se, for example those described in Ullmann's Encyclopedia of Industrial Chemistry, 7th ed., 2013 Electronic Release, chapter: Filtration, 1. Fundamentals and Filtration 2. Equipment. For example, these may be cartridge filters, filter presses, pressure plate filters, bag filters or drum filters. Preference is given to using cartridge filters or pressure plate filters. The filtration can be conducted with or without filtering aids. Suitable filtering aids are filtering aids based on kieselguhr, perlite and cellulose.

Suitable centrifuges and also separators are known to the expert. In process engineering terms, for a centrifugation in the process of the invention, it is possible to use any centrifugation methods and apparatuses known per se, for example those described in Ullmann's Encyclopedia of Industrial Chemistry, 7th ed., 2013 Electronic Release, chapter: Centrifuges, Filtering and Centrifuges, Sedimenting.

The removal of the catalyst can also be effected as an aqueous extraction by addition of water. For this purpose, the product mixture comprising as yet unconverted alkyl (meth)acrylate and any separate azeotroping agent, and also the stabilizer and the catalyst, is contacted with water. It is also possible to conduct two or more washing steps, for example three washing steps. The amount of washing water per washing step is generally 0.1 to 2 times and preferably 0.2 to 0.5 times the amount of product mixture.

The wash can be conducted, for example, in a stirred vessel or in another conventional apparatus, for example in a column or mixer-settler apparatus.

In process engineering terms, for a wash in the process of the invention, it is possible to use any extraction and washing methods and apparatuses known per se, for example those described in Ullmann's Encyclopedia of Industrial Chemistry, 6th ed., 1999 Electronic Release, chapter "Liquid—Liquid Extraction—Apparatus". For example, these may be single-stage or multistage, preferably single-stage, extractions and also extractions in cocurrent or countercurrent mode.

The washed reaction mixture is optionally admixed with a storage stabilizer, such that the desired concentration of stabilizer, for example 100 ppm, is attained in the target product. This concentration, which is adjustable as desired by this method, depends on the particular specification of the end product and for commercial alkyl (meth)acrylates, for example, is in the range from 15 to 200 ppm. The storage stabilizers used are generally stabilizers selected from the group of the phenols, for example 2,6-di-tert-butyl-4-methylphenol, 6-tert-butyl-2,4-dimethylphenol, hydroquinone and hydroquinone monomethyl ether, preferably hydroquinone monomethyl ether.

Subsequently, in a distillation step (v), unconverted alkyl (meth)acrylate and any separate azeotroping agent, and also any water, are distilled out of the product mixture. This distillation is generally effected at a temperature of 40° C. to 100° C., preferably 60° C. to 80° C., and a variable pressure of 2 to 700 mbar. In addition, these components may also be removed by stripping with a gas, preferably an oxygenous gas.

The distillative removal is effected, for example, in a stirred tank with jacket heating and/or internal heating coils under reduced pressure.

It will be appreciated that the distillation can also be effected in a falling-film or thin-film evaporator. To this end, the reaction mixture is passed through the apparatus, preferably repeatedly in circulation, under reduced pressure, for example at 20 to 700 mbar, preferably 30 to 500 mbar and more preferably from 50 to 150 mbar, and a temperature of 40 to 80° C.

An inert gas, preferably an oxygenous gas and more preferably air or a mixture of air and nitrogen (lean air), may advantageously be introduced into the distillation apparatus, for example 0.1 to 1, preferably 0.2 to 0.8 and more preferably 0.3 to 0.7 $m^3/m^3$ h, based on the volume of the reaction mixture.

Performance of steps (iv) and (v) leaves a product in the form of a bottom product having the above-described purity.

The invention also provides for the use of isosorbide di(meth)acrylate as resin component for two-pack adhesive compositions.

Two-pack adhesive compositions of the invention for chemical securing technology comprise
I. a synthetic resin having a viscosity at 23° C. between 100 and 10 000 (mPa·s), comprising the isosorbide di(meth)acrylate, and
II. a hardener for the synthetic resin.

One component of the adhesive composition of the invention is a synthetic resin having a viscosity (at 23° C.) between 100 and 10 000, preferably 200 to 2000 and especially 500 to 1500 mPa·s, measured in the absence of fillers. It comprises the isosorbide di(meth)acrylate.

The synthetic resin may comprise 2% to 20% by weight of other curable resins, such as polyester, vinyl ester, bismaleimide or epoxy resins, and, for the purpose of the impact modification, 2% to 20% by weight of a thermoplastic such as polyamide or polyester or a rubber.

If accelerators are required for peroxide curing, their position is appropriately together with the resin, i.e. separately from the hardener. Suitable accelerators are: aromatic amines such as N,N-dimethylaniline, N,N-diethylaniline; toluidines and xylidines such as N,N-diisopropylidene-para-toluidine, N,N-dimethyl-p-toluidine, N,N-bis(2-hydroxyethyl)xylidine; and also Co salts, Mn salts, Sn salts or Ce salts, for example cobalt naphthenate, and mixtures of amine accelerators and cobalt accelerators. The accelerators are generally present in the synthetic resin in amounts of preferably 0.5% to 5% by weight.

In general, the supply form of a two-chamber cartridge is chosen. Cartridges used are preferably two-chamber cartridges wherein the larger chamber comprises the resin and the smaller chamber the hardener. The larger chamber has a volume about 5 to 10 times greater than the smaller chamber.

In the chamber comprising the synthetic resin component, it is additionally also possible for fillers to be present. Reinforcing fillers used for the adhesive composition are, for example, quartz, glass, corundum, porcelain, earthenware, heavy spar, light spar, talc and chalk. The fillers are added in the form of sands, flours or specific shaped bodies (cylinders, spheres, etc.), either to the resin solution and/or to the hardener (initiator). The fillers can be used in the form of fibers (fibrous fillers). Preference is given to the globular inert substances (in spherical form), which have much stronger strengthening action.

The hardener is provided in a separate position from the resin. Preferred hardeners are organic peroxides that break down at low temperatures. Of particularly good suitability are benzoyl peroxide and methyl ethyl ketone peroxide, and also tert-butyl perbenzoate, cyclohexanone peroxide, lauryl peroxide and cumene hydroperoxide, and also mixtures of various peroxides. The peroxides are preferably used in amounts of 0.5% to 10% by weight, preferably of 1% to 5% by weight. The hardeners are appropriately applied to inert fillers, preference being given to quartz sands having particle sizes of 0.5 to 3 mm or of 3 to 6 mm in terms of dimensions.

In the case of foamable adhesive compositions, carbonate is appropriately added to the resin; the acid component can be introduced into a chamber either together with the hardener or else into a separate, third chamber.

The two-pack adhesive composition of the invention can be used as a plugging compound for securing anchorages in drillholes. Anchorages of this kind have good crack propagation characteristics, low shrinkage stress and excellent adhesion on mineral receiving materials, such as concrete and natural stone, and on foam and cavity blocks.

The invention is more particularly described using the examples which follow.

EXAMPLES

Example 1

Isosorbide (5110 g, 35.0 mol) was reacted with 3 equivalents of ethylene oxide (4620 g, 105 mol) and catalytic amounts of KOH (48.3 g, 0.863 mol) at 160 to 180° C. in a pressure reactor at not more than 5 bar. After the reaction had ended, the product was cooled down and neutralized with acetic acid.

Example 2

Transesterification of Isosorbide*3EO in the Presence of Potassium Phosphate

The transesterification was effected with introduction of air in a 750 mL jacketed reactor equipped with an anchor stirrer, an air inlet, a separating column and a liquid divider. This apparatus was initially charged with 200 g of isosorbide3E0 (OH number 415 mg KOH/g), 0.06 g of methylhydroquinone (MEHQ) and 600 g of methyl methacrylate (MMA, stabilized with 15 ppm of MEHQ) at room temperature. 9.4 g of potassium phosphate were added and the reaction mixture was heated at a bath temperature of 80° C., which was adjusted to 100° C. over the course of the reaction. A pressure of 300 mbar (abs.), 400 mbar later, was established and an azeotrope of methanol and MMA was distilled off continuously, in the course of which the bottom temperature rose from 60° C. to 80° C. The reflux ratio was 2:1, and later 10:1 (reflux:output). After the reaction had ended, the product was filtered through a paper filter and the reaction mixture was concentrated under reduced pressure. The reaction product has an OH number of 2 mg KOH/g, corresponding to <0.5% alcohol calculated as residual isosorbide*3EO alcohol, or 1.2% calculated as monomethacrylate of isosorbide*3EO (all figures are % by weight, unless stated otherwise).

Comparative Example 1

Transesterification of Isosorbide in the Presence of Potassium Phosphate

The transesterification was effected in a 1.6 L jacketed reactor equipped with an anchor stirrer, an air inlet, a separating column and a liquid divider. The reflux ratio was 10:1, and later 10:3 (reflux:output), the stirrer speed was 180 rpm and the air introduction rate was 1.5 L/h. This apparatus was initially charged with 175 g of isosorbide, 0.48 g of methylhydroquinone (MEHQ) and 1200 g of methyl methacrylate (MMA, stabilized with 15 ppm of MEHQ) at room temperature. 19.1 g of potassium phosphate were added and the reaction mixture was heated at a bath temperature of 80° C., which was adjusted to 100° C. over the course of the reaction. A pressure of 400 mbar (abs.) was established and an azeotrope of methanol and MMA was distilled off continuously, in the course of which the bottoms temperature rose from 75° C. to 82° C. After the reaction had ended, the product was filtered through a paper filter and the reaction mixture was concentrated under reduced pressure. The reaction mixture has the following composition (in GC area %): isosorbide (0%), sum total of monomethacrylates (4.3%), sum total of by-products 10% (no further analysis), dimethacrylate target product (>85.7%).

Comparative Example 2

Esterification of Isosorbide*3EO

A 1 L four-neck flask equipped with a thermometer, stirrer, water trap and air inlet was initially charged with cyclohexane (96 g), isosorbide*3E0 (271 g; OH number 415 mg KOH/g), MeHQ (0.34 mg), 50% hypophosphorous acid (0.84 g) and Cu(II) acetate solution (5%, 3 g). Subsequently, methacrylic acid was metered in (120 g, stabilized with 200 ppm of MEHQ). Methanesulfonic acid (9.6 g) was added. The mixture was heated. After 3 h 40 min, a further 69 g of methacrylic acid were metered in. Over the course of the reaction, a portion of the cyclohexane was removed by distillation. Water was distilled over at an internal temperature of 83 to 108° C. After 12 h, the reaction was stopped. After cooling, the reaction mixture was admixed with 200 mL of cyclohexane and with 15% sodium chloride solution, with NaOH solution and once more with 15% sodium chloride solution. After phase separation, the organic phase was concentrated under reduced pressure. The reaction product had an OH number of 16 mg KOH/g, corresponding to 3.9% alcohol calculated as residual isosorbide*3EO alcohol, or 9.7% calculated as monomethacrylate of isosorbide*3EO.

Comparative Example 3

Transesterification of Isosorbide*3EO in the Presence of a Ti Catalyst

A 0.75 L flange reactor having a column, condenser, liquid divider, anchor stirrer and air inlet was initially charged with ethyl acrylate (750 g), MeHQ (0.4 g), PTZ (0.04 g) and isosorbide*3EO (340 g; OH number 415.5 mg KOH/g) and heated up at a bath temperature of 95° C. with introduction of air while stirring. At a pressure of 300 mbar, 105 g of ethyl acrylate (EA) were distilled off. 105 g of ethyl acrylate and titanium tetraisopropoxide (14.3 g) were metered in and the mixture was heated up further to bottom temperature 92° C. The reaction mixture was cloudy at first, and clear later. Ethyl acrylate was distilled off with a reflux ratio of 3:1. EA was metered in in portions, in the amounts that corresponded to the EA in the distillate. The bottom temperature rose to 102° C. over the course of the reaction. Bottoms and distillate were sampled at regular intervals to observe the course of the reaction. A vacuum of not more than 925 mbar was applied. After 5 h, the reaction was stopped and the mixture was cooled down.

The reaction mixture was admixed with 25 mL of water, filtered through a paper filter and concentrated under reduced pressure.

The reaction product had an OH number of 27 mg KOH/g, corresponding to 6.5% alcohol calculated as residual isosorbide*3EO alcohol, or 15.6% calculated as monoacrylate of isosorbide*3EO.

Comparative Example 4

Transesterification of Isosorbide*3EO in the Presence of a Ti Catalyst

A 0.75 L flange reactor having a column, condenser, liquid divider, anchor stirrer and air inlet was initially charged with methyl methacrylate (750 g), MeHQ (0.26 g), PTZ (0.03 g) and isosorbide*3E0 (338 g, OH number 415.5 mg KOH/g) and heated up at a bath temperature of 95° C. with introduction of air while stirring. At a pressure of 300 mbar, 105 g of methyl methacrylate were distilled off. 105 g of methyl methacrylate and titanium tetraisopropoxide (14.2 g) were metered in and the mixture was heated up further to bottom temperature 98° C. The reaction mixture was cloudy at first, and clear later. Methyl methacrylate was distilled off with a reflux ratio of 10:3, and later 5:3. Methyl methacrylate was metered in in portions, in the amounts that corresponded to the methyl methacrylate in the distillate. The bottom temperature rose to 105° C. over the course of the reaction. Bottoms and distillate were sampled at regular intervals to observe the course of the reaction. A vacuum of not more than 900 mbar was applied. After 12 h, the reaction was stopped and the mixture was cooled down.

The reaction mixture was admixed with 30 mL of water, filtered through a paper filter and concentrated under reduced pressure.

The reaction product has an OH number of 21 mg KOH/g, corresponding to 5.1% alcohol calculated as residual isosorbide*3E0 alcohol, or 12.7% calculated as monomethacrylate of isosorbide*3EO.

Comparative Example 5

Transesterification of Isosorbide*3EO in the Presence of an Sn Catalyst

A 0.75 L flange reactor having a column, condenser, liquid divider, anchor stirrer and air inlet was initially charged with ethyl acrylate (481 g), MeHQ (0.61 g), PTZ (0.61 g), cyclohexane (89 g), dimethyltin dichloride (0.46 g), 30% sodium methoxide solution in methanol (0.32 g) and isosorbide*3EO (406 g, OH number 415.5 mg KOH/g), and the contents were heated up to a bottom temperature of 91° C. with introduction of air while stirring. After boiling had commenced, a reflux ratio of 20:1 was established, which was varied over the course of the reaction to down to 2.1. Ethyl acrylate and cyclohexane were metered in in portions, in a corresponding manner to the amounts distilled off.

The bottom temperature rose to 106° C. over the course of the reaction. Bottoms were sampled at regular intervals to observe the course of the reaction.

After 21 h, the experiment was stopped. The reaction product has an OH number of 44 mg KOH/g, corresponding to 10.6% alcohol calculated as residual isosorbide*3EO alcohol, or 25.5% calculated as monoacrylate of isosorbide*3EO.

The invention claimed is:

1. A process for preparing isosorbide ethoxylate di(meth)acrylate by transesterifying alkyl (meth)acrylate with isosorbide ethoxylate, the process comprising:
    (i) ethoxylating isosorbide to obtain isosorbide ethoxylate,
    (ii) reacting alkyl (meth)acrylate with isosorbide ethoxylate in the presence of potassium phosphate as a catalyst and a stabilizer and in the presence of an azeotroping agent which forms an azeotrope with alcohol bound in the alkyl (meth)acrylate,
    (iii) continuously distilling off the azeotrope of the azeotroping agent and alcohol, wherein (ii) and (iii) are conducted simultaneously until the isosorbide ethoxylate has been essentially fully converted,
    (iv) removing the catalyst from a product mixture comprising isosorbide ethoxylate di(meth)acrylate, and
    (v) distilling unconverted alkyl (meth)acrylate and the azeotroping agent out of the product mixture.

2. The process according to claim 1, wherein the azeotroping agent is the alkyl (meth)acrylate.

3. The process according to claim 1, wherein the azeotroping agent is a separate solvent other than alkyl (meth)acrylate.

4. The process according to claim 3, wherein the azeotroping agent is at least one agent selected from the group consisting of n-heptane and cyclohexane.

5. The process according to claim 1, wherein the alkyl (meth)acrylate is methyl or ethyl (meth)acrylate.

6. The process according to claim 1, wherein the stabilizer is hydroquinone monomethyl ether.

7. The process according to claim 1, wherein the alcohol is removed from the azeotrope of an entraining agent and alcohol distilled off in (iii) by washing with water and the azeotroping agent is recycled into a reaction vessel.

8. The process according to claim 1, wherein, after (v), an isosorbide ethoxylate di(meth)acrylate having a content of secondary components of <4% by weight is obtained.

9. The process according to claim 8, wherein, after (v), an isosorbide ethoxylate di(meth)acrylate having a content of secondary components of <2% by weight is obtained.

* * * * *